(12) United States Patent
Golden et al.

(10) Patent No.: US 9,241,483 B2
(45) Date of Patent: *Jan. 26, 2016

(54) FAST-ACTING DISINFECTANT COMPOSITIONS FOR REDUCING OR ELIMINATING MICROBIAL POPULATIONS

(75) Inventors: Jeffry Golden, Creve Coeur, MO (US); Paul Brister, O'Fallon, MO (US)

(73) Assignee: Contec, Inc., Spartanburg, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/537,632

(22) Filed: Jun. 29, 2012

(65) Prior Publication Data

US 2014/0004208 A1    Jan. 2, 2014

(51) Int. Cl.
*A01N 31/02* (2006.01)
*A01N 37/16* (2006.01)
*A01N 43/36* (2006.01)
*A01N 59/00* (2006.01)

(52) U.S. Cl.
CPC ............... *A01N 31/02* (2013.01); *A01N 37/16* (2013.01); *A01N 43/36* (2013.01); *A01N 59/00* (2013.01)

(58) Field of Classification Search
CPC .... A01N 43/90; A01N 2300/00; A01N 25/30
See application file for complete search history.

(56) References Cited

U.S. PATENT DOCUMENTS

| | | | |
|---|---|---|---|
| 5,035,859 A * | 7/1991 | Gu et al. | 422/28 |
| 5,451,346 A * | 9/1995 | Amou et al. | 252/186.23 |
| 5,587,358 A | 12/1996 | Sukigara | |
| 5,776,919 A | 7/1998 | Sukigara | |
| 6,627,593 B2 | 9/2003 | Hei | |
| 6,692,694 B1 | 2/2004 | Curry et al. | |
| 7,150,412 B2 | 12/2006 | Wang et al. | |
| 7,462,590 B2 * | 12/2008 | Tichy et al. | 510/372 |
| 7,569,181 B2 | 8/2009 | Golden | |
| 7,776,362 B2 | 8/2010 | Qian et al. | |
| 8,030,372 B2 | 10/2011 | Rosing et al. | |
| 8,110,538 B2 | 2/2012 | Martin et al. | |
| 8,142,715 B2 | 3/2012 | Curry et al. | |
| 8,383,205 B2 | 2/2013 | Rosing et al. | |
| 2003/0072720 A1 | 4/2003 | Nevo | |
| 2003/0175216 A1 | 9/2003 | Rosenberg | |
| 2006/0229225 A1 * | 10/2006 | Martin et al. | 510/375 |
| 2009/0285871 A1 * | 11/2009 | Cunningham et al. | 424/405 |

FOREIGN PATENT DOCUMENTS

| | | |
|---|---|---|
| EP | 1343867 B1 | 12/2001 |
| WO | 02050241 A2 | 12/2001 |
| WO | 2011005270 A1 | 1/2011 |

OTHER PUBLICATIONS

Togashi, et al., "Antibacterial Activity of Long-Chain Fatty Alcohols Against *Staphylococcus Aureus*", ISSN 1420-3049, Molecules 2007, 12, 139-148.

* cited by examiner

*Primary Examiner* — Frederick Krass
*Assistant Examiner* — Tracy Liu

(57) ABSTRACT

In one embodiment, a disinfectant composition includes a peroxide, a peracid, an anionic surfactant, a nonionic polymer, and one or both of a linear fatty alcohol and an alkyl pyrrolidone. The disinfectants provide greater killing rates for microbial populations in short periods of time, and therefore can be considered to be fast-acting disinfectants.

27 Claims, 3 Drawing Sheets

FAST-ACTING DISINFECTANT COMPOSITIONS FOR REDUCING OR ELIMINATING MICROBIAL POPULATIONS

BACKGROUND

Fast-acting disinfectants are important for reducing or eliminating microbial populations in a wide range of settings. In many instances, it is desirable for a disinfectant to achieve a particular microbicidal efficacy within a relatively short contact time. By way of example, a desirable disinfectant may reduce the microbial population on a surface, in a liquid, or in a substance by a desired number of logs (powers of ten) within a contact time of a minute or two, or even less.

Unfortunately, many commercially-available disinfectants are either inadequate in terms of microbicidal efficacy or require long contact times to achieve the desired level of killing. It can therefore be appreciated that it would be desirable to have more effective and/or faster acting disinfectants.

BRIEF DESCRIPTION OF THE FIGURES

The present disclosure may be better understood with reference to the following figures.

DETAILED DESCRIPTION

Figure 1:
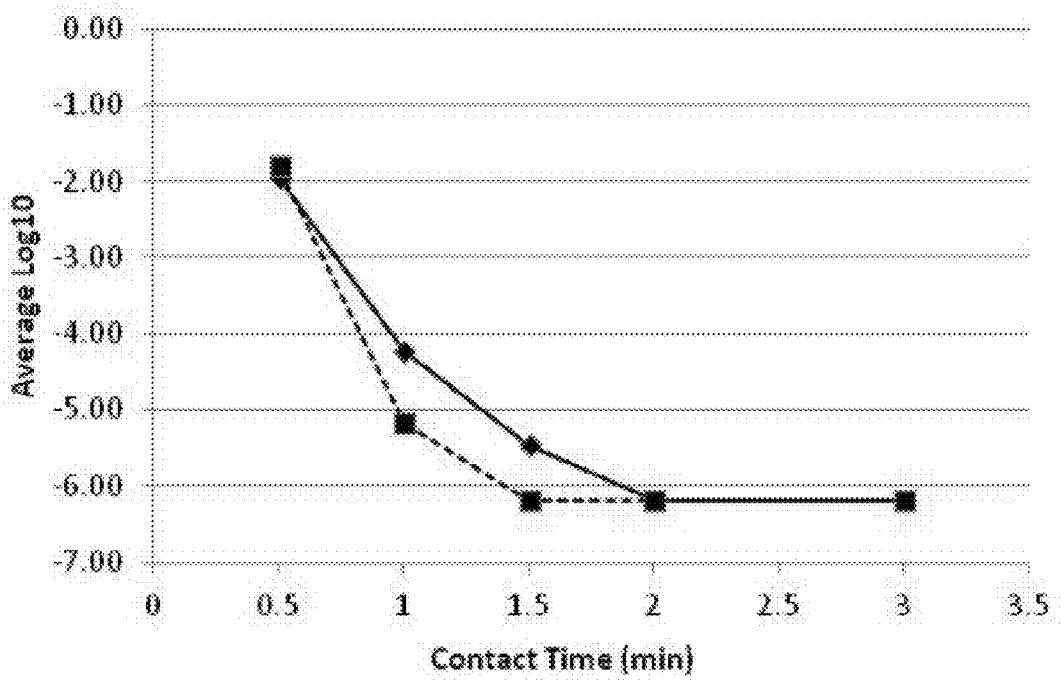
FIG. 1 is a graph that plots the surviving log fraction of a microbial population as a function of contact time for multiple formulations of disinfectant solutions.

As described above, it would be desirable to have more effective and/or faster acting disinfectants. Disclosed herein are disinfectant compositions that provide greater killing rates for microbial populations in short periods of time. In some embodiments, the compositions comprise a peroxide, a peracid, an anionic surfactant, an ionic polymer, and one or more of a linear higher alcohol and an alkyl pyrrolidone. In some embodiments, the compositions demonstrate sporicidal disinfection of *C. difficile* spores with a two-minute contact time, which is a substantial improvement over known disinfectants.

In the following disclosure, various specific embodiments are described. It is to be understood that those embodiments are example implementations of the disclosed inventions and that alternative embodiments are possible. All such embodiments are intended to fall within the scope of this disclosure.
Introduction For regulatory registration and allowance of label claims for killing pathogens that pose a public health threat, antimicrobials such as disinfectants, sporicides, sterilants, decontaminants, fungicides, virucides, sanitizers, and tuberculocides must pass stringent laboratory tests that are required by regulatory agencies, such as the U.S. Environmental Protection Agency (USEPA). For example, a sporicidal disinfectant having a registered claim for killing *C. difficile* spores must demonstrate a required number of logs (e.g., 6 logs) of killing within a particular contact time.

There are compositions that demonstrate good sporicidal efficacy in killing *C. difficile* spores, but the products registered with USEPA have contact times of five minutes or longer to achieve 6 logs reduction. In practice, a five-minute contact time is a significant fraction of the limited time typically allocated for routine cleaning and disinfection of patient rooms, high-contact surfaces, and infection control "hot spots." For terminal cleaning of patient rooms, critical care units, operating rooms, and emergency care facilities, faster-acting disinfectants can enable greater patient throughput and more efficient use of the facility.

Healthcare industry groups have recommended that contact times of a minute or two are desirable so that reapplication of disinfectant is not necessary and removal of excess disinfectant and surface drying can be achieved at an economical pace. Furthermore, if the contact time is much less than the time for evaporation of odiferous volatile components, then exposure to such components can be reduced and improved aesthetic acceptance obtained.

The peracid/peroxide compositions described in U.S. Pat. No. 8,110,538, which is hereby incorporated by reference into the present disclosure, exhibit excellent efficacy in killing microbial populations. However, film integrity and wetting can be issues for such compositions when applied onto hydrophobic materials such as polytetrafluoroethylene materials and acrylonitrile butadiene styrene materials, which are commonly used are electronic devices. In view of these issues, the inventors added surface-active agents in the form of nonionic surfactants and commercial wetting agents containing nonionic surfactants to the peracid/peroxide compositions in an attempt to improve the wetting of such materials. Nonionic surfactants were selected so that there would be minimal interference in the associations formed by a lactam-containing polymer and phosphate ester surfactant of the compositions. As expected, the addition of a wetting agent improved the film-forming and wetting characteristics of the ready-to-use and use dilution embodiments of the peracid/peroxide compositions. Unexpectedly, however, it was discovered that the addition of minute amounts of surface-active agents consistently resulted in a greater killing rate and a corresponding shorter contact time to achieve a desired reduction in microbial population. Although the wetting agent comprised only 0.1 percent weight (w/w %) of the composition, it provided about a ¾ log greater log reduction in quantitative disk carrier test (QDCT) studies with a 60-second contact time. Further experiments revealed that the addition of two particular components of the wetting agent to the peracid/peroxide composition substantially improved the killing rate even when added in very small amounts. These components were alkyl pyrrolidone,n-octyl pyrrolidone (n-alkyl pyrrolidone) and a linear fatty alcohol known as undecanol (also known as undecan-1-ol). N-alkyl pyrrolidone is currently used as a solvent, a non-streaking agent, and a surface active agent, but it is not known as a sporicide or a potentiator of antimicrobial activity in peracid/peroxide compositions. Although undecanol is known to have microbicidal and inhibitory properties of its own at relatively high concentrations of about 5 w/w % or greater, the above-described improvements were surprisingly achieved with concentrations lower than 1 w/w %.
Disinfectant Compositions In some embodiments, the disclosed disinfectant compositions comprise a peroxide, a peracid, an anionic surfactant, a nonionic polymer, and one or more of a linear higher alcohol (also called a linear fatty alcohol) and an alkyl pyrrolidone. In some embodiments, the compositions can include other components, such as fragrances, colorants, deodorants, antifoaming agents, foaming agents, or other commonly used ingredients. The compositions can be ready-to-use (RTU) solutions or concentrate solutions that can be diluted with water to make a use dilution solution prior to application. In some embodiments, the concentrate solution can have a concentration that is 6× the concentration of the RTU solution. In some embodiments, the compositions can be used as a photosensitizer/decontaminant with or without the application of ultraviolet (UV) light.

The peroxide can comprise hydrogen peroxide, hydrogen peroxide donors or adducts, peroxide precursor and activator, and mixtures thereof. In some embodiments, the peroxide is present in the composition in a concentration of approximately 1.0 w/w % to 60.0 w/w %. For RTU compositions, the composition can comprise peroxide in a concentration of approximately 1.0 w/w % to 10.0 w/w %. For concentrate compositions, the composition can comprise peroxide in a concentration of approximately 6.0 w/w % to 60.0 w/w %.

The peracid can comprise one or more of peroxyacetic acid (also called peracetic acid), C1-C4 carboxylic peracids, or peroxyoctanoic acid. Examples of carboxylic peracids include: peroxyformic acid, peroxyacetic acid, peroxypropionic acid, peroxybutanoic acid, peroxypentanoic acid, peroxyhexanoic acid, peroxyheptanoic acid, peroxyoctanoic acid, peroxynonanoic acid, peroxydecanoic acid, peroxyundecanoic acid, peroxydodecanoic acid, or the peroxyacids with their branched chain isomers, peroxylactic acid, peroxymaleic acid, peroxyascorbic acid, peroxyhydroxyacetic acid, peroxyoxalic acid, peroxymalonic acid, peroxysuccinic acid, peroxyglutaric acid, peroxyadipic acid, peroxypimelic acid, peroxysubric acid, and mixtures thereof. In some embodiments, the peracid is present in the composition in a concentration of approximately 0.005 w/w % to 30.0 w/w %. For RTU compositions, the composition can comprise peracid in a concentration of approximately 0.005 w/w % to 5.0 w/w %. For concentrate compositions, the composition can comprise peracid in a concentration of approximately 0.03 w/w % to 30.0 w/w %.

In some embodiments, the peracid concentration is dependent upon the peroxide concentration. For example, for concentrate compositions in which the peroxide concentration is approximately 2.0 w/w % to 5.0 w/w %, the peracid concentration can be approximately 0.1 w/w % to 0.25 w/w %. The use dilution solutions made from such a concentrate composition are the result of dilutions in the range of about ½ (i.e., 1 part water and 1 part concentrate) to about ¹/₁₀ (i.e., 9 parts water and 1 part concentrate). In a concentrate composition in which the peroxide concentration is approximately 20 w/w % to 28 w/w %, the peracid concentration can be approximately 0.9 w/w % to 1.6 w/w %. The use dilution solutions made from such a concentrate composition are the result of dilutions in the range of about ¼ (i.e., 3 parts water and 1 part concentrate) to about ¹/₃₀ (i.e., 29 parts water and 1 part concentrate).

The anionic surfactant can comprise a phosphate ester comprising a hydrophilic polyoxyethylene chain and an R-terminal group selected from the group consisting of a lipophilic alkyl chain and an alkylphenol. In other embodiments, the anionic surfactant contains phosphate ester and comprises a mixture of phosphate monoesters and diesters of nonyl phenol ethoxylate with a hydrophilic polyoxyethylene chain in a range of PEO-3 to PEO-9. Such surfactant is available from Ashland Chemical as OC-20. In still other embodiments, the anionic surfactant contains phosphate ester and comprises a lipophilic alkyl chain in a range of C9 thru C13, and a hydrophilic polyoxyethylene chain in a range of PEO-3 to PEO-9. Such surfactant is available from Ashland Chemical as OC-40 and comprises a mixture of phosphate mono- and di-esters of tri-decyl alcohol ethoxylate. In further embodiments, the anionic surfactant can be a sulfonated anionic surfactant, such as an alpha olefin sulfonate, a substituted alkane-sulfonate, a salt of a linear or branched alkyl sulfate (e.g., with hydrocarbon chain lengths ranging from C6 to C24), an alcohol sulfate, an alcohol ether sulfate, or mixtures thereof.

In some embodiments, the composition can comprise anionic surfactant in a concentration of approximately 0.01 w/w % to 18.0 w/w %. For RTU compositions, the composition can comprise anionic surfactant in a concentration of approximately 0.01 w/w % to 3.0 w/w %. For concentrate compositions in which the peroxoide concentration is approximately 0.06 w/w % to 18.0 w/w %, the anionic surfactant can be present in the composition in a concentration of approximately 0.1 w/w % to 1 w/w %. For concentrate compositions in which the peroxoide concentration is approximately 20 w/w % to 28 w/w %, the anionic surfactant can be present in the composition in a concentration of approximately 0.3 w/w % to 3.0 w/w % or approximately 0.4 w/w % to 1.0 w/w %.

In some embodiments, the anionic surfactant can be a photoreactive surfactant containing phosphate ester so that the surfactant, along with the nonionic polymer, assists in a multifunctional photo-enhanced microbicidal action. The selected anionic photoreactive surfactant and nonionic polymer enable the composition to be used as a photosensitizer for photoreactive microbicidal effect when a surface coated with the composition or liquid containing the composition is illuminated with UV light having a wavelength at or below approximately 31% nanometers (nm).

In some embodiments, the nonionic polymer contains lactam. The polymer forms associations with the anionic surfactant and interacts with the peracid and peroxide by the formation of adducts. The associations and adducts provide additional reactive chemistry that enhances the microbicidal efficacy of the compositions. In some embodiments, the nonionic polymer is polyvinyl pyrrolidone, either as a homopolymer or as a copolymer (also called a heteropolymer). Although they do not possess a lactam group and do not have the interactions/adducts with surfactants, the nonionic polymer can alternatively comprise polyethylene glycol, polypropylene glycol, methyl cellulose, or mixtures thereof.

In some embodiments, the composition can comprise nonionic polymer in a concentration of approximately 0.01 w/w % to 18.0 w/w %. For RTU compositions, the composition can comprise nonionic polymer in a concentration of approximately 0.01 w/w % to 3.0 w/w %. For concentrate compositions, the composition can comprise nonionic polymer in a concentration of approximately 0.06 w/w % to 18.0 w/w %.

Linear fatty alcohols having from 8 to 13 carbon atoms exhibit bactericidal or bacteriostatic properties when used in concentrations of several percent. The mechanisms behind the antimicrobial action of these compounds at such concentrations xdepend upon the number of carbon atoms present in the alcohol. C10 (decanol) and C011 (undecanol) alcohols cause ionic leakage through membranes. With contact times of multiple hours, these alcohols may result in a 2 to 3 log reduction in bacterial population. However, bactericidal action at concentrations less than 0.5% and contact times of a few minutes or less would be expected to be insignificant. At such low concentrations and short contact times, the sporicidal activity of these compounds is expected to be inconsequential. Unexpectedly, however, it was discovered that small concentrations of a linear fatty alcohol can significantly increase the killing rate of peracid/peroxide compositions and lead to greater microbicidal efficacy. In some embodiments, the linear fatty alcohol comprises one or more of decanol and undecanol. Of those alcohols, undecanol may be preferable in some embodiments because it has a more aesthetically pleasing odor and may be less irritating to skin. In other embodiments, the linear fatty alcohol comprises a C8 to C13 alcohol, 1-octanol, 1-nonanol, 11-decanol, 1-undecanol, 1-dodecanol, 1-tridecanol, or mixtures thereof.

In some embodiments, the composition has a linear alcohol concentration of approximately 0.01 w/w % to 0.9 w/w %. For RTU compositions, the composition can comprise a linear alcohol concentration of approximately 0.01 w/w % to 0.15 w/w %. For concentrate compositions, the composition can comprise a linear alcohol concentration of approximately 0.06 w/w % to 0.9 w/w %. Alkyl pyrrolidones are lactam-containing molecules that can act as a surfactant and as a solvent for hydrophobic compounds. Alkyl pyrrolidones can associate with nonionic polymers, especially lactam-containing polymers such as polyvinyl pyrrolidone, and they can also associate with anionic surfactants. N-octyl pyrrolidone and dodecyl pyrrolidone are surfactants with relatively low water solubility (0.12% and 0.004%, respectively) that can be significantly greater in the presence of anionic surfactant. Because of their lactam, these compounds can form adducts with peracids and peroxides. In some embodiments, the alkyl pyrrolidone used in the compositions is n-octyl pyrrolidone. In other embodiments, the alkyl pyrrolidone comprises C8 to C18 alkyl pyrrolidones, such as dodecyl pyrrolidone.

In some embodiments, the alkyl pyrrolidone is present in the composition at a concentration of approximately 0.01 w/w % to 0.9 w/w %. For RTU compositions, the composition can comprise an alkyl pyrrolidone concentration of approximately 0.01 w/w % to 0.15 w/w %. For concentrate compositions, the composition can comprise an alkyl pyrrolidone concentration of approximately 0.06 w/w % to 0.9 w/w %.

As described above, the disinfectant composition can alternatively comprise a linear fatty alcohol or an alkyl pyrrolidone. However, faster and more thorough killing may result when both components are present in the composition. In some embodiments, undecanol and n-octyl pyrrolidone are both present and are added as a mixture to the composition. In such a mixture, the n-octyl pyrrolidone acts as a solubilizing agent for the undecanol. By way of example, the n-octyl pyrrolidone can be in a concentration of approximately 0.01 w/w % to 0.05 w/w %, and the undecanol can be in a concentration of approximately 0.01 w/w % to 0.05 w/w %.

Linear fatty alcohols and alkyl pyrrolidone can be found in some commercial products. For example, the wetting agent EasyWet®-20 is a nonionic surfactant comprising a linear undecyl alcohol ethoxylate (poly(oxy-1,2-ethanediyl), alpha-undecyl-omega-hydroxy-, CAS number 34398-01-1, in a concentration in the range of 30-70%), a small amount of anionic surfactant (sulfuric acid monododecyl ester sodium salt, CAS number 151-21-3, in a concentration in the range of 1-2%), 1-octyl 2-pyrrolidone (CAS number 2687-94-7, in a concentration in the range of 15-25%), and undecanol (CAS number 112-42-5, in a concentration in the range of 5-15%). In some embodiments, the disinfectant composition comprises a peracid, a peroxide, an anionic surfactant, a nonionic polymer, and EasyWet®-20 as a means of adding a undecanol and n-octyl pyrrolidone to the composition.

When used as an aqueous solution, the disinfectant compositions comprise a balance of water. In some embodiments, the water is de-ionized so that it has a low trace metals content. In embodiments in which longer shelf life (e.g., one year or more) is desired, the water can be deionized and reverse osmosis treated. In some embodiments, the transition metal content is less than 500 parts-per-billion (ppb) or 100 ppb. For example, concentrations of copper, iron, zinc, magnesium, silver, and nickel can be less than 100 ppb for multi-year shelf life and storage stability.

Storage-stable compositions can be obtained by mixing the ingredients at or near equilibrium concentrations at room temperature. The composition is mixed and equilibrated at elevated temperature and then cooled and re-equilibrated at room, use, or storage temperature. After mixing the ingredients, the linear fatty alcohol and/or the n-octyl pyrrolidinone (or a wetting agent containing these ingredients) can be added to the composition. An example process for making a storage-stable composition is described in the following paragraphs.

In one embodiment of a process for making a batch of a storage-stable embodiment of the compositions comprises selecting process ingredients including a relatively concentrated solution of peracetic acid, hydrogen peroxide, and acetic acid, a relatively concentrated solution of hydrogen peroxide, glacial acetic acid, phosphate ester surfactant, water soluble polymer containing lactam, little or no additional stabilizer, and optionally small amounts of acid catalyst such as sulfuric acid and minors such as fragrance and colorants are combined in a specified order and in precise amounts to form a more dilute solution with peracetic acid at concentration greater than the desired final concentration of peracetic acid and reacted at elevated temperature to obtain with accuracy an equilibrium or near-equilibrium very dilute composition with concentrations of active ingredients that are storage stable within regulatory limits for more than one year.

The process accurately makes a batch of a storage stable microbicidal composition comprising a very dilute peracetic acid solution with the resulting composition having an equilibrium concentration quotient of about $$K_c \approx 1.4\exp\left(240.7\left(\frac{1}{T} - \frac{1}{293.2}\right)\right)$$

between about 283 and about 328 degrees Kelvin and the mole fraction of water of the said resulting composition is greater than about 0.9. In one embodiment, the process comprises the following steps:

(1) selecting target concentrations of hydrogen peroxide, peracetic acid, polymer, and surfactant in the resulting composition at a selected batching temperature in the range of about 40° C. to about 55° C.;

(2) calculating the target equilibrium concentration of acetic acid in the resulting composition;

(3) selecting an initial concentration of peracetic acid;

(4) determining by calculation that includes the decomposition of some of the peracetic acid into acetic acid and oxygen and the evaporation of some of the water during the batch process, and optionally, the degradation of some of the peracetic acid, acetic acid, and hydrogen peroxide, the amount of a diluted solution of a more concentrated solution of known composition, designated the peracetic acid stock solution, comprising peracetic acid, hydrogen peroxide, acetic acid, acid catalyst, and water, the amount of glacial acetic acid of known concentration, the amount of an aqueous solution of hydrogen peroxide of known concentration, designated the hydrogen peroxide stock solution, the amounts of surfactant, polymer, and minors, and the amount of de-ionized/reverse osmosis filtered water to be added to the batch to obtain the target concentrations;

(5) heating about 75% to about 100% of the amount of de-ionized/reverse osmosis filtered water in a clean, passivated blending vessel to the said selected batching temperature and continuously mixing the contents of the said vessel to limit the spatial temperature variation of the said contents to less than about 5° C.;

(6) adding the determined amount of water soluble polymer to and mixing with the said heated water;

(7) adding the determined amount of surfactant, linear fatty alcohol, and/or acyl pyrrolidones to and mixing with the contents of the vessel;

(8) adding the determined amounts of hydrogen peroxide solution and glacial acetic acid to and mixing with the contents of the vessel;

(9) adding the determined amount of peracetic acid solution to and mixing with the contents of the vessel;

(10) adding the remainder of the said determined amount of water to and mixing with the contents of the vessel;

(11) maintaining the contents of the vessel at the batching temperature with less than about 5° C. spatial or temporal variation in the temperature of the said contents for a batching time in the range of about 2 to 4 equilibration times;

(12) measuring the concentrations of hydrogen peroxide, peracetic acid, and optionally acetic acid;

(13) optionally adjusting the composition of the blended mixture to obtain the target concentrations;

(14) optionally adding one or more said minor ingredients to and mixing with the contents of the vessel;

(15) cooling the contents of the contents of the vessel to a desired temperature or to ambient temperature in a time that is much less than an equilibration time, and optionally adding one or more said minor ingredients to and mixing with the contents of the vessel; and

(16) optionally storing the resulting composition in the vessel, or transferring the said contents to another or several vessels, or transferring the said contents to product packages, or transferring the said contents as an ingredient in one or more products.

Testing

Testing was performed to evaluate the efficacy of the above-described compositions in killing microbial populations. More particularly, testing was performed to determine the effect of the addition of one or more components to peracid/peroxide disinfectant compositions. The tests and their results are presented below in the following examples.

EXAMPLE 1

In a first test, a commercial disinfectant known as PeridoxRTU® was compared with a mixture of PeridoxRTU® plus the commercial wetting agent EasyWet®-20 in terms of their efficacies in killing *Bacillus subtilis* spores. The PeridoxRTU® comprised approximately 0.23 w/w % peracetic acid, approximately 4.4 w/w % hydrogen peroxide, approximately 0.1 w/w % anionic surfactant (OC-40), an equilibrium quantity of acetic acid, and approximately 0.1 w/w % polyvinyl pyrolidone. The composition for the EasyWet®-20 was described above.

The tests were conducted according to the QDCT protocol and ASTM E2197-11 ("Standard Quantitative Disk Carrier Test Method for Determining the Bactericidal, Virucidal, Fungicidal, Mycobactericidal and Sporicidal Activities of Liquid Chemical Germicides"), and the test substances were neutralized with catalase and thiosulfate neutralizer. Recovered untreated controls amounted to approximately $1.5 \times 10^6$ spores/carrier. Thus, the level of detection (LOD) amounted to 6.2 logs of reduction.

The results of the tests are provided in FIG. 1. In that figure, the surviving log fraction (i.e., the negative of the log reduction) of a microbial population is shown as a function of the contact time for the PeridoxRTU® (solid line) and PeridoxRTU® plus the addition of 0.1 w/w % of EasyWet®-20 (dashed line). As is apparent from FIG. 1, the composition including the EasyWet®-20 killed approximately 5.2 logs in one minute as compared to PeridoxRTU® alone, which killed approximately 4.2 logs in one minute.

EXAMPLE 2

In further testing, PeridoxRTU®, PeridoxRTU® diluted by a factor of two with water, an adjusted formulation of PeridoxRTU® with reduced peracetic acid and acetic acid, PeridoxRTU® with 0.2 w/w % of fragrance added, and a use dilution of Peridox® concentrate were used to kill *Bacillus subtilis* spores. The adjusted formulation of PeridoxRTU® comprised 4.95 w/w % hydrogen peroxide, 0.11 w/w % peracetic acid, an equilibrium quantity of acetic acid, 0.1 w/w % of OC-40, 0.1 w/w % polyvinyl pyrrolidone, and a balance of water. The use dilution of Peridox® concentrate comprised 4.0 w/w % hydrogen peroxide, 0.2 w/w % peracetic acid, 0.3 w/w % acetic acid, 0.1 w/w % of OC-40, 0.1 w/w % polyvinyl pyrrolidone, and a balance of water.

The tests were conducted according to the same QDCT protocol and ASTM E2197-11 described above in relation to Example 1. The test substances were neutralized with catalase and thiosulfate neutralizer. Recovered untreated controls amounted to approximately $1.3 \times 10^6$ spores/carrier. The LOD amounted to approximately 6.1 logs of reduction.

Figure 2:
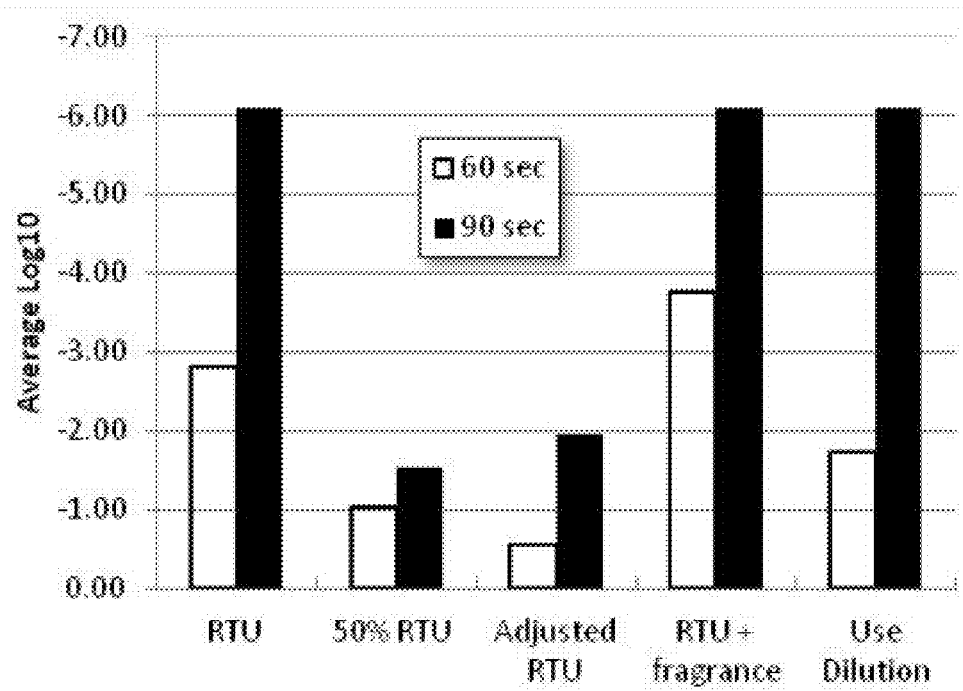
FIG. 2 is a graph that plots the surviving log fraction of a microbial population after a 60-second and a 90-second contact time for multiple formulations of disinfectant solutions.

The results of the tests are provided in FIG. 2. In that figure, the surviving log fraction of the microbial population is shown for contact times of 60 seconds and 90 seconds. As can be appreciated from the figure, the PeridoxRTU® ("RTU"), PeridoxRTU® with 0.2 w/w % of fragrance added ("RTU+ fragrance"), and the use dilution of Peridox® concentrate ("Use Dilution") exhibited the greatest efficacy in killing *Bacillus subtilis* spores.

EXAMPLE 3

In still other testing, each of PeridoxRTU®, PeridoxRTU® plus 0.1 w/w % EasyWet®-20, PeridoxRTU® diluted by a factor of two with water, PeridoxRTU® diluted by a factor of two with water plus 0.1 w/w % EasyWet®-20, the adjusted formulation of PeridoxRTU® described above, the adjusted formulation of PeridoxRTU® described above plus 0.1 w/w % EasyWet®-20, PeridoxRTU® with 0.2 w/w % of fragrance added, PeridoxRTU® with 0.2 w/w % of fragrance added plus 0.1 w/w % EasyWet®-20, the use dilution of Peridox® concentrate described above, and the use dilution of Peridox® concentrate plus 0.1 w/w % EasyWet®-20 were individually used to kill *Bacillus subtilis* spores with a 60-second contact time.

The tests were conducted according to the same QDCT protocol and ASTM E2197-11 described above in relation to Example 1. The test substances were neutralized with catalase and thiosulfate neutralizer. Recovered untreated controls amounted to about $1.3 \times 10^6$ spores/carrier. The LOD amounted to about 6.1 logs of reduction.

Figure 3:
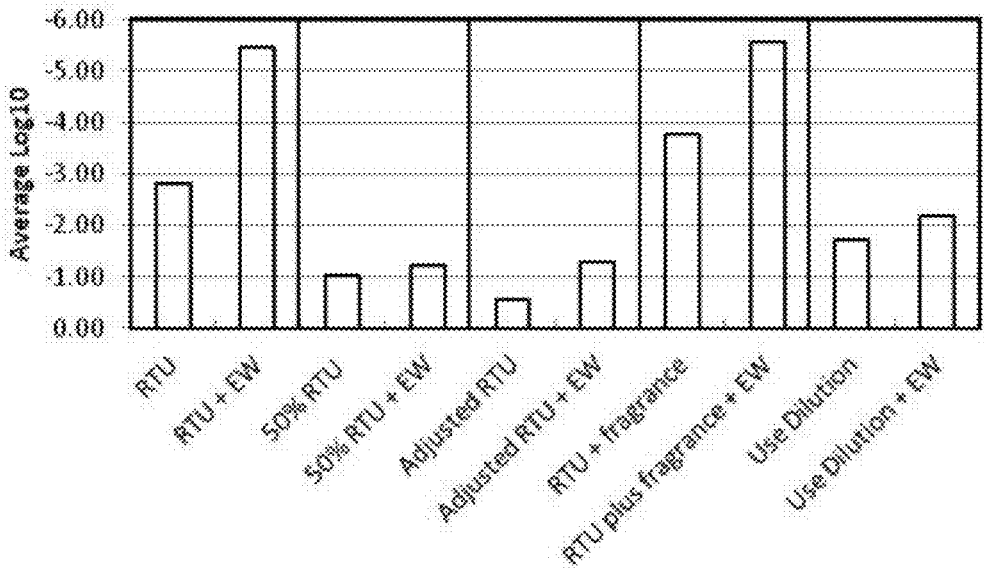
FIG. 3 is a graph that plots the surviving log fraction of a microbial population after a 60-second contact time for multiple formulations of disinfectant solutions.

The results of the testing are shown in FIG. 3. As is apparent from that figure, the compositions containing EasyWet®-20 exhibited greater kill rates.

EXAMPLE 4

In still further testing, multiple formulations of disinfectant compositions were tested to determine their efficacy in killing Bacillus subtilis spores with a 60-second contact time. The formulations included: PeridoxRTU® with 0.05 w/w % poly (oxy-1,2-ethanediyl, alpha-undecyl omega-hydroxy-("RTU+A"); PeridoxRTU® with 0.015 w/w % undecan-1-ol ("RTU+B"); PeridoxRTU® with 0.01 w/w % sulfuric acid monododecyl ester sodium salt ("RTU+C"); PeridoxRTU® with 0.020 w/w % 1-octyl-2-pyrrolidinone ("RTU+D"); PeridoxRTU® with 0.05 w/w % poly(oxy-1,2-ethanediyl, alpha-undecyl omega-hydroxy-) and with 0.020 w/w % 1-octyl-2-pyrrolidinone ("RTU+A and D"); a formulation of PeridoxRTU® having no peracetic acid or peroxide active ingredients to which 0.1 w/w % poly(oxy-1,2-ethanediyl, alpha-undecyl omega-hydroxy-) was added ("No Active+A"); a formulation of PeridoxRTU® having no peracetic acid or peroxide active ingredients to which 0.1 w/w % undecan-1-ol was added ("No Active+B"); a formulation of PeridoxRTU® having no peracetic acid or peroxide active ingredients to which 0.1 w/w % sulfuric acid monododecyl ester sodium salt was added ("No Active+C"); a formulation of PeridoxRTU® having no peracetic acid or peroxide active ingredients to which 0.1 w/w % 1-octyl-2-pyrrolidinone was added ("No Active+D"); PeridoxRTU® ("RTU"); and PeridoxRTU® plus EasyWet®-20 ("RTU+EW").

The tests were conducted according to the same QDCT protocol and ASTM E2197-11 described above in relation to Example 1. The test substances were neutralized with catalase and thiosulfate neutralizer. Recovered untreated controls amounted to about $1.6 \times 10^6$ spores/carrier. The LOD amounted to about 6.2 logs of reduction.

Figure 4:
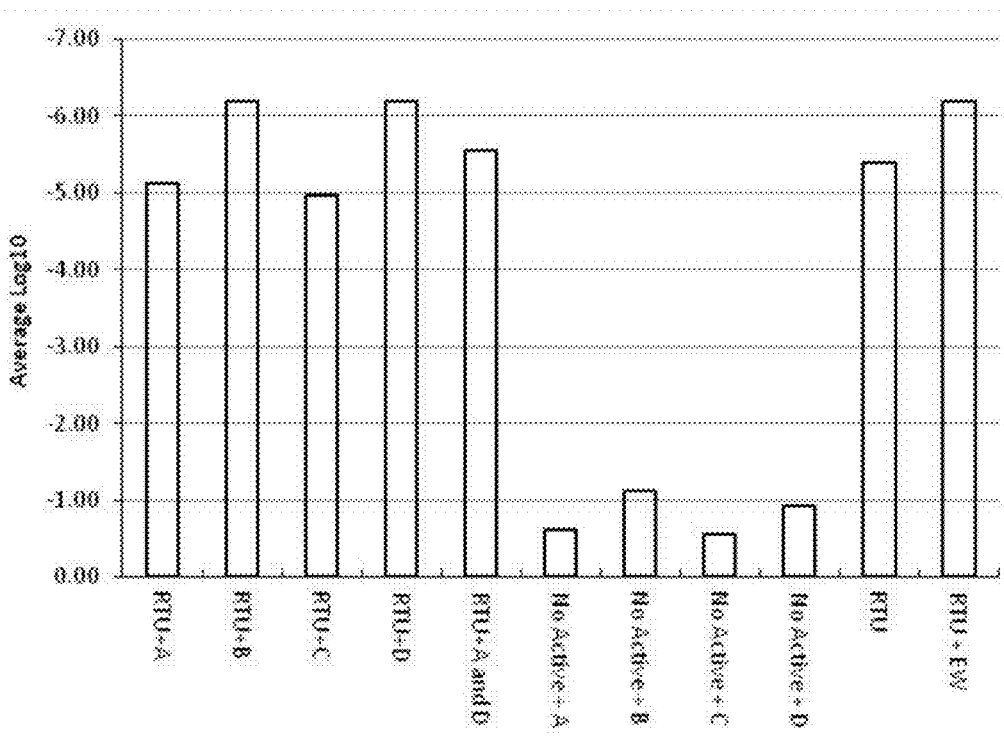
FIG. 4 is a graph that plots the surviving log fraction of a microbial population after a 60-second contact time for multiple formulations of disinfectant solutions.

The results of the testing are shown in FIG. 4. As is apparent from that figure, the peracid/peroxide compositions including undecan-1-ol, the 1-octyl-2-pyrrolidinone, and the EasyWet®-20 provide faster killing of *Bacillus subtilis* spores.

EXAMPLE 5

In additional testing, further formulations of disinfectant compositions were tested to determine their efficacy in killing *Bacillus subtilis* spores with a 60-second contact time. The formulations included: PeridoxRTU® with 0.05 w/w % poly (oxy-1,2-ethanediyl, alpha-undecyl omega-hydroxy-) ("RTU+A"); PeridoxRTU® with 0.05 w/w % poly(oxy-1,2-ethanediyl, alpha-undecyl omega-hydroxy-) and 0.015 w/w % undecan-1-ol ("RTU+A+B"); PeridoxRTU® with 0.015 w/w % Undecan-1-ol and 0.020 w/w % 1-octyl-2-pyrrolidinone ("RTU+B+D"); PeridoxRTU® with 0.015 w/w % Undecan-1-ol, 0.01 w/w % sulfuric acid monododecyl ester sodium salt, and 0.020 w/w % 1-octyl-2-pyrrolidinone ("RTU+B+C+D"); PeridoxRTU® ("RTU"); and PeridoxRTU® plus 0.1 w/w % EasyWet®-20 ("RTU/EW").

The tests were conducted according to the same QDCT protocol and ASTM E2197-11 described above in relation to Example 1. The test substances were neutralized with catalase and thiosulfate neutralizer. Recovered untreated controls amounted to about $2.6 \times 10^6$ spores/carrier. The LOD amounted to about 6.4 logs of reduction.

Figure 5:
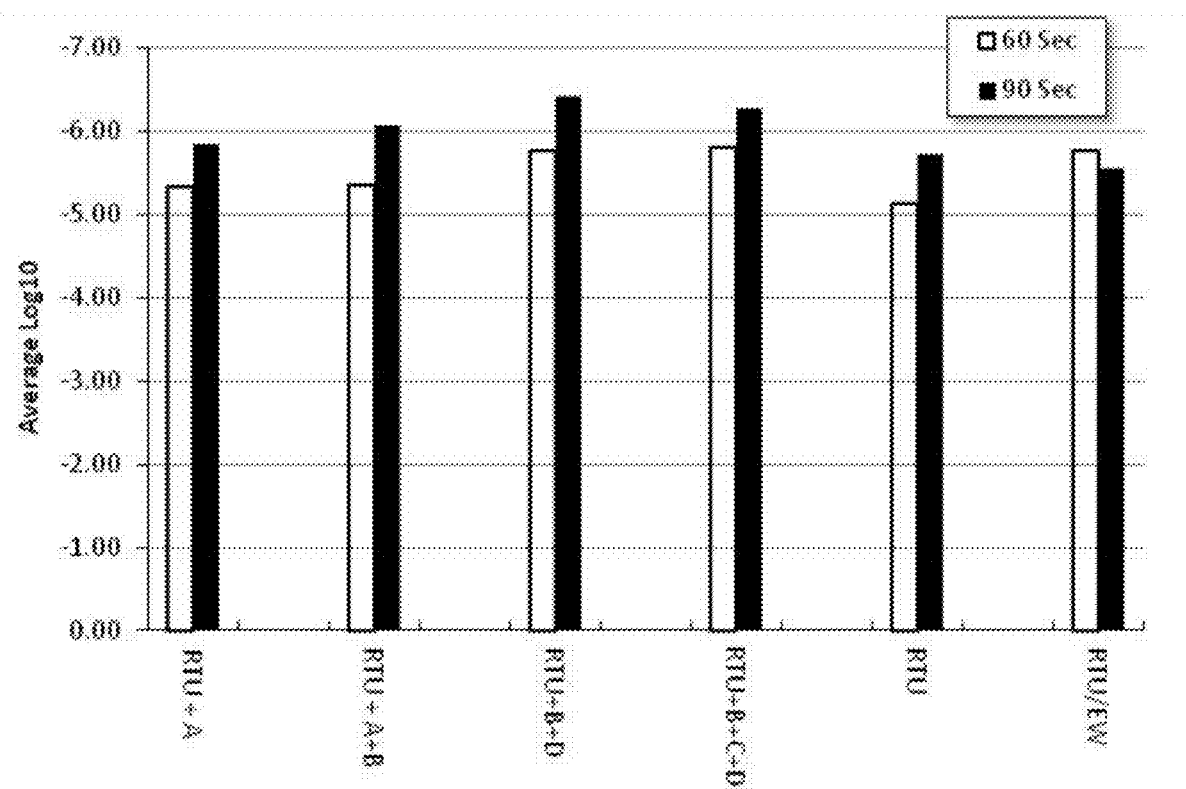
FIG. 5 is a graph that plots the surviving log fraction of a microbial population after a 60-second contact time for multiple formulations of disinfectant solutions.

The results of the testing are shown in FIG. 5. As is apparent from that figure the combination of undecan-1-ol and the 1-octyl-2-pyrrolidinone in the peracid/peroxide compositions provided the fastest killing rates.

EXAMPLE 6

Tests were also performed at an independent laboratory (ATS Labs, Inc., Eagan, Minn.) to determine the microbicidal efficacy of PeridoxRTU® with 0.1 w/w % of EasyWet®-20 versus PeridoxRTU® alone for killing *C. difficile* spores. The tests were performed in accordance with good laboratory practice (GLP) and using the QDCT protocol and ASTM E2197-11 described above in relation to Example 1. PeridoxRTU® alone demonstrated greater than 6.3 logs of killing to the level of detection (no surviving spores detected) with a contact time of three minutes, and 5.5±0.4 logs of killing with a LOD of 6.3 logs with a two-minute contact time. In contrast, PeridoxRTU® with 0.1 w/w % of EasyWet®-20 demonstrated greater than 6.4 logs of killing with a contact time of two minutes and with a LOD of 6.5 logs.

EXAMPLE 7

Tests for virucidal efficacy were also performed using MS-2 bacteriophage as the test organism and according to the QDCT protocol and ASTM E2197-11 described above in relation to Example 1. After a two-minute contact time, PeridoxRTU® demonstrated 4.99 logs of killing, and PeridoxRTU® with 0.1 w/w % of EasyWet®-20 demonstrated greater than 5.67 logs of killing with a LOD of 6.47 logs.

Applications

The disclosed compositions can be used in many applications. For example, the compositions can be used as a disinfectant, sporicide, sporidical disinfectant, sterilant, decontaminant, fungicide, virucide, sanitizer, tuberculocide, moldicide, or mildewcide. The compositions have use as an antimicrobial on hard, non-porous surfaces; on painted surfaces and on sealed masonry, concrete, and cinder block; and on and in porous materials such as textiles, unpainted drywall, and carpet. The compositions are suitable for use in a variety of settings, including healthcare, veterinary, child-care, agricultural, food production, distribution, sale, educational, recreational, residential, correctional, institutional, commercial, industrial, military, emergency response, counter-terrorism, and laboratory settings.

As is apparent from the test data, the compositions have fast acting microbicidal action and, in particular, sporicidal action. In addition, the compositions have good material compatibility properties, meaning that they are non-corrosive or have very low corrosivity to most materials and therefore are not damaging to most materials. These properties make them well suited for use as chemical sterilants for medical, veterinary, horticultural, and agricultural implements.

The compositions are also suitable for use as decontaminants for killing biowarfare and bioterrorism agents and can be used without the application of UV light. In some embodiments, however, the compositions can be used as a photosensitizer/decontaminant, in which case they are applied and then illuminated with UV light. When used as photosensitizer and subsequently illuminated with UV light, the compositions can be used to destroy or deactivate nucleic acid compounds, such as deoxyribonucleic acid.

When diluted with water, the concentrated compositions can be used as use dilutions that can be applied to surfaces; sprayed into volumes such as enclosed spaces, partially enclosed spaces, or into aerosol clouds; added to pre-saturated wipes; or combined with liquids or with absorbent, granular, or porous materials. The compositions can be applied by liquid or aerosol spraying, which may be as an electrostatically sprayed aerosol; by wiping; by mopping; by pouring; by immersion; by flowing; by pumping; or by other methods.

Several specific embodiments have described in the foregoing disclosure. Various modifications can be made to those embodiments without departing from the scope of the disclosure. It is therefore intended that all matter contained in the foregoing description and shown in the accompanying drawings shall be interpreted as illustrative rather than limiting. Therefore, the breadth and scope of the disclosure should not be limited by any of the above-described exemplary embodiments, but should be defined only in accordance with the following claims appended hereto and their equivalents.

The invention claimed is:

1. A disinfectant composition comprising:
a peroxide;
a peracid;
an anionic surfactant;
a nonionic polymer;
a linear fatty alcohol present at a concentration of approximately 0.01% w/w and 0.9% w/w, wherein the linear fatty alcohol is a C8 to C13 linear fatty alcohol; and
an alkyl pyrrolidone wherein said composition demonstrates sporicidal disinfection of *C. difficile* or *Bacillus subtilis* spores with two minute contact time.

2. The composition of claim 1, wherein the peroxide is selected from the group consisting of hydrogen peroxide, a hydrogen peroxide donor or adduct, a peroxide precursor and activator, and mixtures thereof.

3. The composition of claim 1, wherein the peroxide is present in a concentration of approximately 1.0 w/w % to 60.0 w/w %.

4. The composition of claim 1, wherein the composition is a ready-to-use composition and the peroxide is present in a concentration of approximately 1.0 w/w % to 10.0 w/w %.

5. The composition of claim 1, wherein the composition is a concentrate composition and the peroxide is present in a concentration of approximately 6.0 w/w % to 60.0 w/w %.

6. The composition of claim 1, wherein the peracid is selected from the group consisting of peracetic acid, a C1-C4 carboxylic peracid, peroxyoctanoic acid, and mixtures thereof.

7. The composition of claim 1, wherein the peracid is present in a concentration of approximately 0.005 w/w % to 30.0 w/w %.

8. The composition of claim 1, wherein the composition is a ready-to-use composition and the peracid is present in a concentration of approximately 0.005 w/w % to 5.0 w/w %.

9. The composition of claim 1, wherein the composition is a concentrate composition and the peracid is present in a concentration of approximately 0.03 w/w % to 30.0 w/w %.

10. The composition of claim 1, wherein the anionic surfactant is selected from the group consisting of a phosphate ester, a sulfonated anionic surfactant, a substituted alkanesulfonate, a salt of a linear or branched alkyl sulfate, an alcohol sulfate, an alcohol ether sulfate, and mixtures thereof.

11. The composition of claim 1, wherein the anionic surfactant is present in a concentration of approximately 0.01 w/w % to 18.0 w/w %.

12. The composition of claim 1, wherein the composition is a ready-to-use composition and the anionic surfactant is present in a concentration of approximately 0.01 w/w % to 3.0 w/w %.

13. The composition of claim 1, wherein the composition is a concentrate composition and the anionic surfactant is present in a concentration of approximately 0.06 w/w % to 18.0 w/w %.

14. The composition of claim 1, wherein the nonionic polymer is selected from the group consisting of polyvinyl pyrrolidone, polyethylene glycol, polypropylene glycol, methyl cellulose, and mixtures thereof.

15. The composition of claim 1, wherein the nonionic polymer is present in a concentration of approximately 0.01 w/w % to 18.0 w/w %.

16. The composition of claim 1, wherein the composition is a ready-to-use composition and the nonionic polymer is present in a concentration of approximately 0.01 w/w % to 3.0 w/w %.

17. The composition of claim 1, wherein the composition is a concentrate composition and the nonionic polymer is present in a concentration of approximately 0.06 w/w % to 18.0 w/w %.

18. The composition of claim 1, wherein the composition is a ready-to-use composition and the linear fatty alcohol is present in a concentration of approximately 0.01 w/w % to 0.15 w/w %.

19. The composition of claim 1, wherein the composition is a concentrate composition and the linear fatty alcohol is present in a concentration of approximately 0.06 w/w % to 0.9 w/w %.

20. The composition of claim 1, wherein the alkyl pyrrolidone is selected from the group consisting of n-octyl pyrrolidone, dodecyl pyrrolidone, and mixtures thereof.

21. The composition of claim 1, wherein the alkyl pyrrolidone is present in a concentration of approximately 0.01 w/w % to 0.9 w/w %.

22. The composition of claim 1, wherein the composition is a ready-to-use composition and the alkyl pyrrolidone is present in a concentration of approximately 0.01 w/w % to 0.15 w/w %.

23. The composition of claim 1, wherein the composition is a concentrate composition and the alkyl pyrrolidone is present in a concentration of approximately 0.06 w/w % to 0.9 w/w %.

24. The composition of claim 1, wherein the linear fatty alcohol and an alkyl pyrrolidone and each is present in a concentration of approximately 0.01 w/w % to 0.05 w/w %.

25. A disinfectant composition comprising:
a peroxide present in a concentration of approximately 1.0 w/w % to 60.0 w/w %;
a peracid present in a concentration of approximately 0.005 w/w % to 30.0 w/w %;
an anionic surfactant present in a concentration of approximately 0.01 w/w % to 18.0 w/w %;
a nonionic polymer present in a concentration of approximately 0.01 w/w % to 18.0 w/w %;
a linear fatty alcohol; wherein the linear fatty alcohol is a C8 to C13 linear fatty alcohol; and
an alkyl pyrrolidone;
wherein both the linear fatty alcohol and the alkyl pyrrolidone are present in a concentration of approximately 0.01 w/w % to 0.05 w/w % wherein said composition demonstrates sporicidal disinfection of *C. difficile* or *Bacillus subtilis* spores with two minute contact time.

26. The composition of claim 25, wherein the alkyl pyrrolidone is selected from the group consisting of n-octyl pyrrolidone, dodecyl pyrrolidone, and mixtures thereof.

27. A method of making a disinfectant composition comprising:
adding a peroxide to an aqueous solution to a concentration of approximately 1.0 w/w % to 60.0 w/w %;
adding a peracid to the solution to a concentration of approximately 0.005 w/w % to 30.0 w/w %;
adding an anionic surfactant to the solution to a concentration of approximately 0.01 w/w % to 18.0 w/w %;
adding a nonionic polymer to the solution to a concentration of approximately 0.01 w/w % to 18.0 w/w %; and
adding a linear fatty alcohol and an alkyl pyrrolidone to the solution to a concentration of approximately 0.01 w/w % to 0.05 w/w %, where the linear fatty alcohol is a C8 to C13 alcohol wherein said composition demonstrates sporicidal disinfection of *C. difficile* or *Bacillus subtilis* spores with two minute contact time.

* * * * *